US006926008B1

(12) United States Patent
Levitt

(10) Patent No.: US 6,926,008 B1
(45) Date of Patent: Aug. 9, 2005

(54) SNORE RELIEF BELT

(76) Inventor: Harold O. Levitt, 128 N. Craig St. Apt. 710, Pittsburgh, PA (US) 15213

(*) Notice: Subject to any disclaimer, the term of this patent is extended or adjusted under 35 U.S.C. 154(b) by 12 days.

(21) Appl. No.: 10/815,537

(22) Filed: Apr. 1, 2004

(51) Int. Cl.[7] .............................................. A61F 5/56
(52) U.S. Cl. ....................... 128/848; 128/845; 128/869; 602/67; 602/19
(58) Field of Search ............................ 128/848, 100.1, 128/101.1, 845, 875, 869, DIG. 15, 98.1; 602/5, 23, 61, 62, 67, 75, 19, 902; 2/319, 2/338; 224/662

(56) References Cited

U.S. PATENT DOCUMENTS

| | | | | |
|---|---|---|---|---|
| 5,207,635 A | * | 5/1993 | Richards et al. | 602/19 |
| 5,429,587 A | * | 7/1995 | Gates | 602/19 |
| 5,645,080 A | * | 7/1997 | Toso | 128/876 |
| 5,651,763 A | * | 7/1997 | Gates | 602/19 |
| 6,137,675 A | * | 10/2000 | Perkins | 2/338 |
| 6,289,893 B1 | | 9/2001 | Levitt | |
| 6,331,170 B1 | * | 12/2001 | Ordway | 602/19 |
| 6,427,697 B1 | * | 8/2002 | Pearcey | 128/876 |
| 6,681,974 B2 | * | 1/2004 | Rotter | 224/662 |
| 6,755,799 B2 | * | 6/2004 | Toda | 602/19 |

* cited by examiner

Primary Examiner—Fadi H. Dahbour

(57) ABSTRACT

The present invention is a unique device for ensuring side sleeping to alleviate snoring. It is more dependable and comfortable than any previous invention for remedying snoring and mild sleep apnea. It lessens airway blockage caused by collapse of the soft throat tissues and the back of the tongue due to gravity by preventing a person from sleeping in the supine position where the worst snoring occurs. The design of the present device is fundamentally different from all prior art invented for this purpose. The present invention comprises an elongated polyurethane foam diaphragm with compressible, preferably polyethylene foam, stop blocks attached to its outer surface at opposite lateral sides, all contained in a fabric main enclosure which is wrapped around a person's body. Cushion sleeves of the same or similar material, containing polyurethane foam pads, are attached to each lateral side of the fabric main enclosure and joined together at the front of the person's body by Velcro or other positive means. An external, detachable friction band of soft stretchable material is attached to the body side of the device to prevent rotation of the person's body within the device.

7 Claims, 3 Drawing Sheets

SNORE RELIEF BELT

BACKGROUND OF THE INVENTION

1. Field of Endeavor

This invention relates principally to mechanical sleep aids, specifically to a comfortable, lightweight device which is secured to one's body to prevent sleeping on one's back where the worst snoring occurs due to soft tissues in the throat collapsing and blocking the airway. When a sleeping person wearing this device attempts to roll from a side to a supine position, the present invention acts immediately to resist the rolling motion while remaining in position comfortably on the person's body all night.

The present invention will aid those persons who snore loudly enough to wake themselves and/or to annoy a sleeping partner. It will also help to alert those whose sleep quality is not improved by alleviation of snoring to seek proper medical treatment.

Another significant benefit is the avoidance of heart and lung damage to those whom it prevents from sleeping in the supine position. It will also serve to make sleep apnea oral prostheses more effective by lessening the pull of gravity on throat tissues caused by sleeping in the supine position. Finally, it will aid compliance by Continuous Positive air pressure (C-Pap) users by lowering the maximum pressure needed when the gravity factor is lessened.

2. Description of Prior Art

Sleep clinics have often recommended an altered T-shirt having a vertical rear pocket encasing one or more tennis balls to prevent sleeping on one's back. This and similar devices seldom achieve the desired objective. The T-shirt usually doesn't fit snugly enough to prevent the tennis balls from shifting out of position.

A more serious disadvantage is that the tennis balls are not compressed until a back-reclining position is reached at which point they do not provide sufficient resistance to remaining on one's back. A more recent approach, the present inventor's previously patented device, the Snore Reducer Jacket (U.S. Pat. No. 6,289,893 issued Sep. 19, 2001) does not consistently resist rolling into the supine position and lacks anti-slip provisions nor is it comfortable all night.

SUMMARY OF THE INVENTION

The present invention, the Snore Relief Belt, differs substantially from this inventor's previous invention, the Snore Reducer Jacket. The earlier invention comprises a fabric-enclosed hard plastic, flexible panel with a pair of laterally separated, hard resistor bars attached to the panel's inner surface.

It maintains a gap between each resistor bar and one's body. Attempting to roll toward one's back closes the nearest gap which causes the corresponding resistor bar to impinge upon the body to resist the rolling. That configuration proved to be inconsistent in preventing rolling toward the supine position and provided little resistance to rotation of one's body within the device.

In contrast, the present invention features an elongated, compressible, low density, preferably polyurethane foam, diaphragm overlaid or laminated with a medium density polyurethane foam backup bar, to which are attached high density, preferably hard polyethylene foam, stop blocks. These elements are contained inside of a fabric main enclosure externally lined on the body side with anti-slip material.

This construction imparts a radically different action of the present from the earlier device. The stop blocks are attached to the outer surface of the backup bar as opposed to the attachment of resistor bars to the surface of the panel in the earlier invention. The stop blocks are shaped so as to apply a concentrated force digging into the bed surface when one attempts to roll toward the supine position. This causes a reacting distributed pressure on the person's body.

This pressure is less severe but more effective in preventing the body from rolling than the direct force of the earlier device.

Unlike the earlier device, which is secured to the body by a two-piece elastic belt and a shoulder strap harness, the present device is secured by a pair of internally padded, overlapping, cushion sleeves also externally lined with anti-slip material on the body side.

The present invention, when snugly wrapped around the body has no gaps and does not need a shoulder strap harness to prevent downward slippage, as does the previous invention. The person's body is surrounded by anti-slip material to provide resistance to rotation of the person's body inside of the device after the reacting pressure stops the external rolling action. There are no belt loops required on the present invention because, instead of the less comfortable elastic bands of the earlier device, there are overlapping foam-filled cushion sleeves. Finally, due to the use of lighter materials and the lesser number of components, the present invention weighs substantially less and can be produced more economically than the more complex earlier device.

DESCRIPTION OF THE DRAWINGS

These features and advantages will be understood in light of the following drawings.

DETAILED DESCRIPTION OF THE INVENTION

Figure 2:
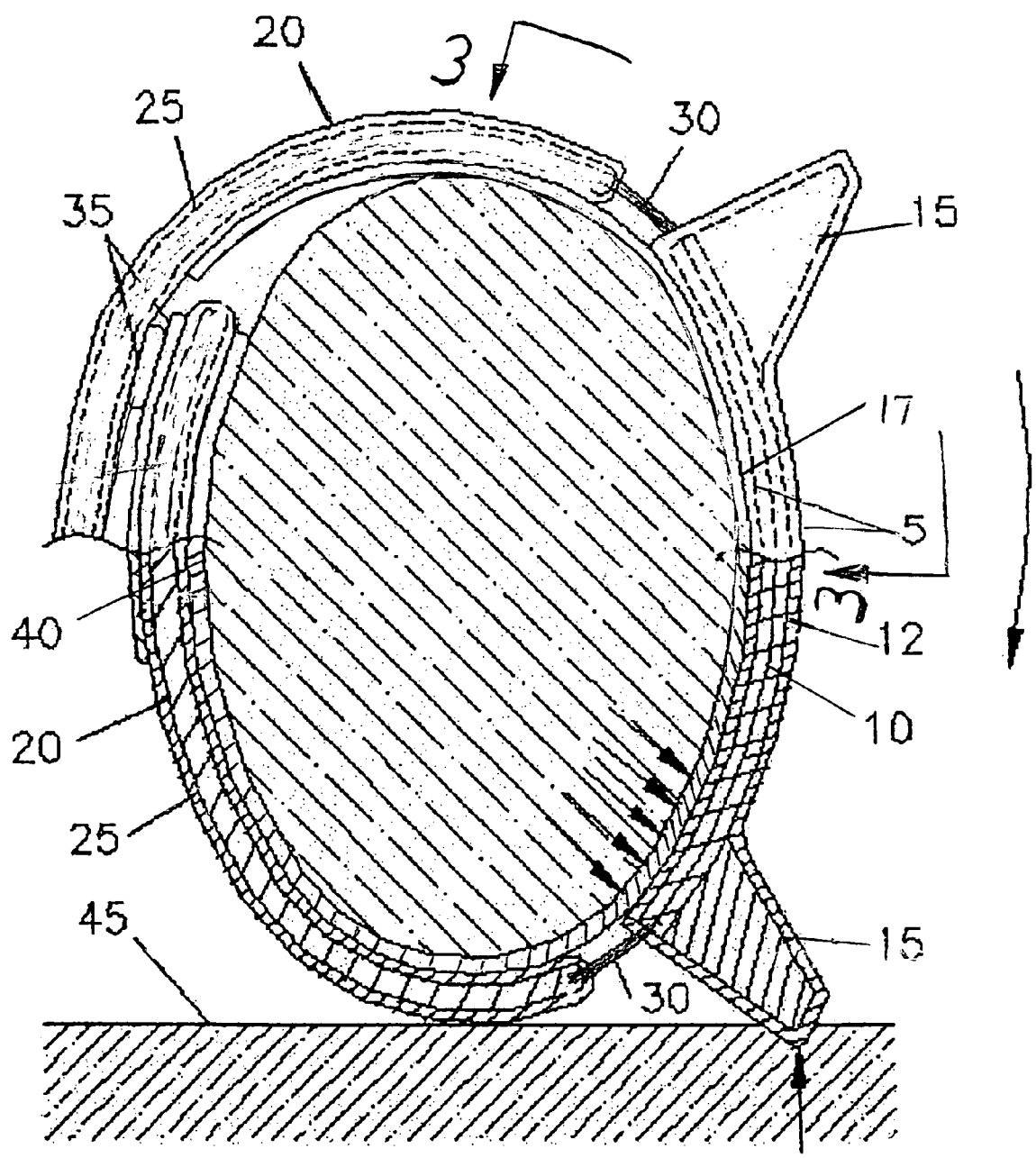
FIG. 2 is a sectional view taken at cutting plane 2—2 of FIG. 1 and rotated clockwise (per the curved arrow) so that one stop block contacts the bed surface.

Referring to FIG. 2, the internal assembly (curved diaphragm 10, over-lying curved backup bar 12 and stop blocks 15) is enclosed by the fabric main enclosure 5, which has a rear overlapped seam 7 (FIGS. 3 and 4) across its width.

Figure 3:
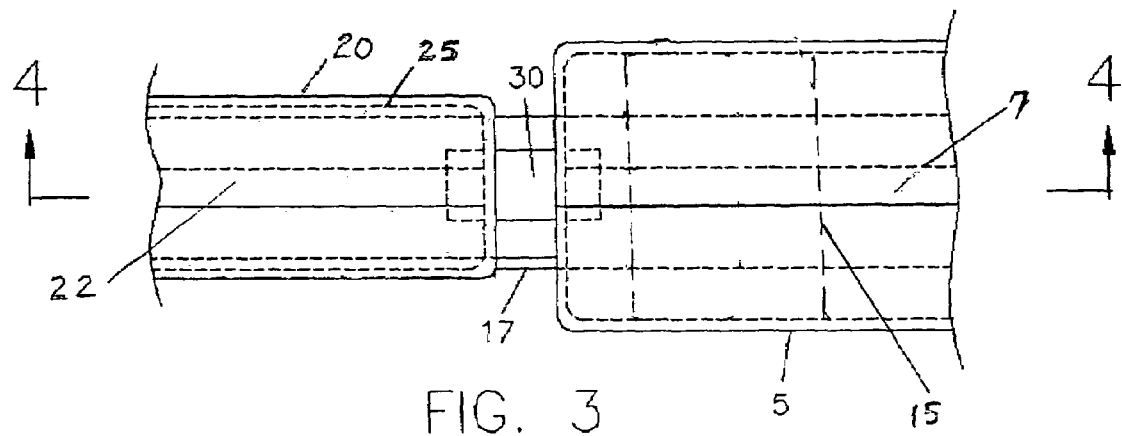
FIG. 3 is a side view of the unwrapped device taken at viewing plane 3—3 of FIG. 2.
Figure 4:
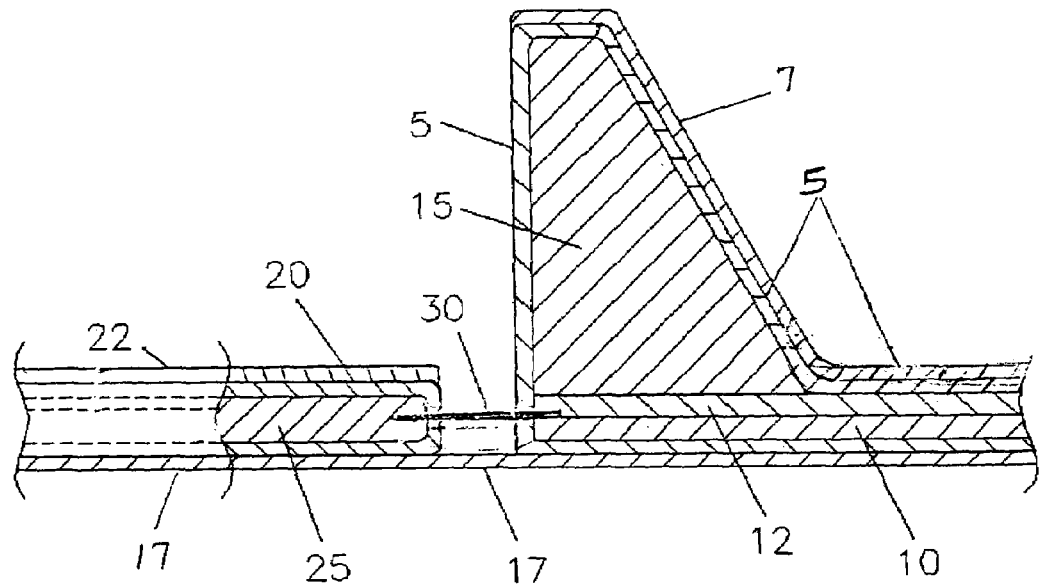
FIG. 4 is a partial sectional view taken at cutting plane 4—4 of FIG. 3.

Friction band 17, (FIGS. 1–4) of non-allergenic material such as soft nylon, lines the body-side surface to resist the body's rotation inside of the device. Cushion sleeves 20 (FIGS. 1–4) enclose soft, compressible, low-density polyurethane pads 25. Each cushion sleeve 20 has an overlapped opening 22 (FIGS. 2–4).

Figure 1:
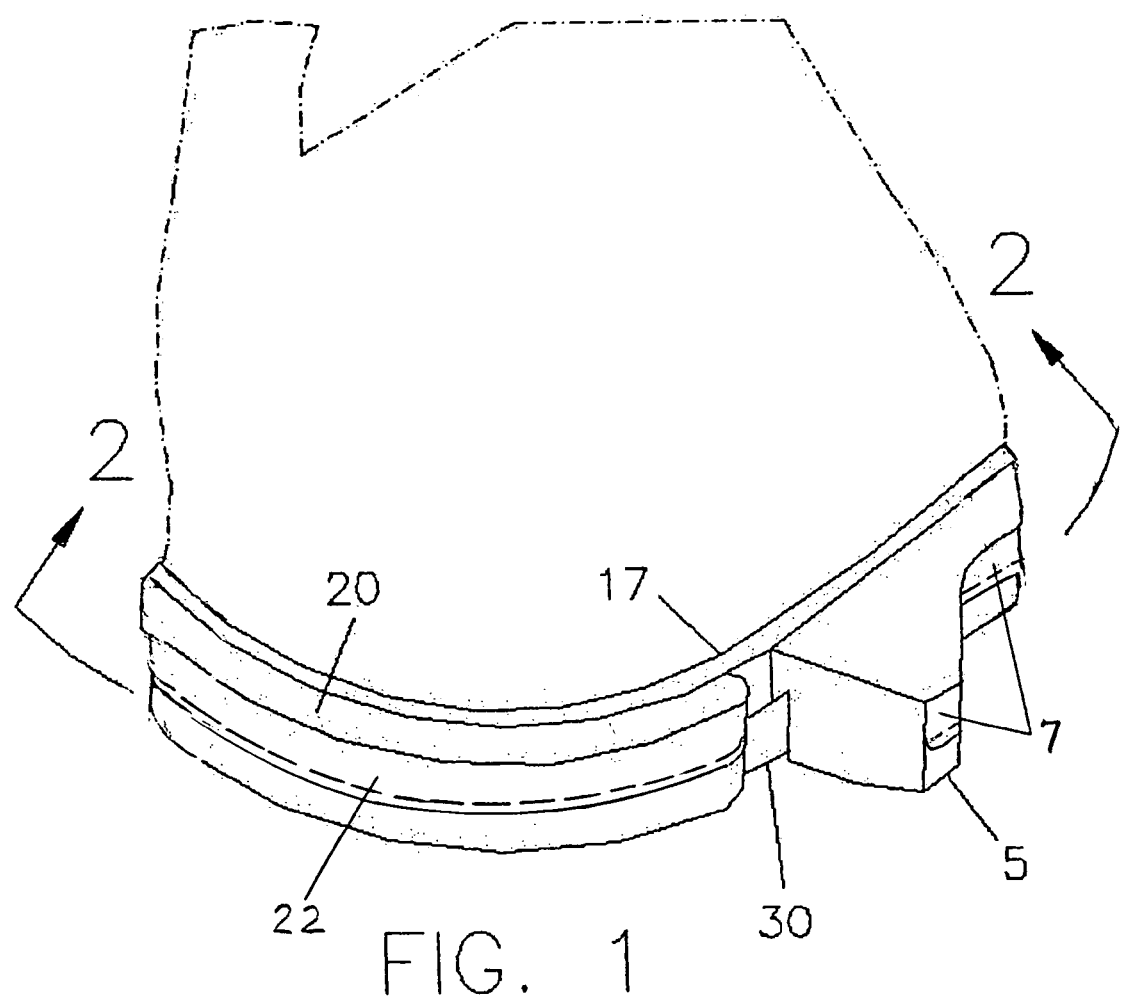
FIG. 1 is a perspective view of the device wrapped around a person's body.

Elastic bands 30 (FIGS. 1–4) connect sleeves 20 to the lateral sides of enclosure 5. The overlapping front ends of sleeves 20 (FIG. 2) are connected, preferably by Velcro strips 35. FIGS. 1 and 2, show the assembled device wrapped around a person's body. The person, while lying on his/her side, fastens cushion sleeves 20 together loosely and rotates the Snore Relief Belt so that one of the stop blocks 15 contacts the mattress. Then cushion sleeves 20 are unfastened and the adjusted device is re-fastend snugly around the person's body. When the person attempts to roll from a side-reclining toward a back reclining-position, in the direction of the curved arrow (FIG. 2), stop block 15 digs into the mattress, causing a concentrated reaction force on the stop block (as indicated by the upward pointing arrow). This creates an equal and opposite distributed reaction pressure between the person's body and friction band 17 (as indicated by the group of downward pointing arrows). The reacting force against stop block 15 and resulting pressure on the persons body are increased as the rolling attempt continues, firmly resisting the rolling motion, Friction band 17 opposes rotation of one's body inside of the device, helping to compel the person to remain in the side-sleeping position. The present invention is thus more dependable and effective than any prior art, including this inventor's previously patented device.

The external elements, consisting of main enclosure 5, cushion sleeves 20 and detachable friction band 17 may be laundered for further use after the internal assembly is removed from main enclosure 5 and pads 25 from cushion sleeves 20.

While the present invention has been described in terms of the preferred embodiment, other similar embodiments may be used for performing the same function. Therefore, the present invention should be construed in breadth and scope in accordance with the recitation of the appended claims.

What is claimed is:

1. A uniquely effective and comfortable device to ensure side-sleeping by preventing a person from rolling toward a back-supported position, where snoring and sleep apnea often occurs due to airway blockage, said device comprising:

an elongated fabric main enclosure containing internal parts which can be inserted or removed through an adequate opening in said enclosure;

a rectangular compressible, layered or laminated diaphragm of foam material located within said enclosure;

compressible stop blocks formed of resilient, high density foam material attached to the rear surface of said diaphragm at the opposite lateral sides;

fabric cushion sleeves, containing removable internal foam pads, and attached to said fabric main enclosure to secure said device snugly around the body.

2. The device according to claim 1 wherein a detachable external friction band of soft stretchable material is attached to the body side to prevent rotation of the person's body inside of the device.

3. The device according to claim 1 wherein the front ends of said cushion sleeves are overlapped and connected together.

4. The device according to claim 1 wherein the rear ends of said cushion sleeves are connected to the lateral sides of said enclosure by elastic transition pieces.

5. The device according to claim 1 wherein said diaphragm and sleeves are compressed comfortably all around the said person's body.

6. The device according to claim 1 wherein said stop blocks provide restraint when one attempts to roll from a side to a back-supported position.

7. The device according to claim 1 which can be disassembled so that the external components can be separated from the inner components and laundered.

\* \* \* \* \*